(12) United States Patent
Harttig et al.

(10) Patent No.: US 8,448,866 B2
(45) Date of Patent: May 28, 2013

(54) ANALYTE DISPOSABLE MEANS AND DEVICE FOR READING INFORMATION

(75) Inventors: Herbert Harttig, Neustadt (DE); Hans List, Hesseneck-Kailbach (DE); Bernd Roesicke, Mannheim (DE); Gerrit Kocherscheidt, Heidelberg (DE); Bruno Thoes, Quierschied (DE); Jean-Michel Asfour, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 119 days.

(21) Appl. No.: 12/197,806

(22) Filed: Aug. 25, 2008

(65) Prior Publication Data
US 2009/0212109 A1      Aug. 27, 2009

(30) Foreign Application Priority Data

Feb. 25, 2006 (EP) ..................................... 06003880

(51) Int. Cl.
*G06K 7/10* (2006.01)

(52) U.S. Cl.
USPC ............ 235/462.05; 235/462.09; 235/462.08; 235/462.1; 235/462.13

(58) Field of Classification Search
USPC ............. 235/462.01, 462.05, 462.09, 462.08, 235/462.1, 462.11, 462.13, 462.32, 462.41, 235/462.42, 462.43, 486, 375, 435, 439, 235/454, 494, 487
See application file for complete search history.

(56) References Cited

U.S. PATENT DOCUMENTS

| | | | | |
|---|---|---|---|---|
| 4,105,926 A | * | 8/1978 | Reno et al. ..................... | 250/566 |
| 4,197,088 A | * | 4/1980 | Meserol et al. ............... | 436/528 |
| 4,263,504 A | | 4/1981 | Thomas | |
| 4,282,425 A | | 8/1981 | Chadima, Jr. et al. | |
| 4,400,353 A | * | 8/1983 | Meserol et al. ................. | 422/73 |
| 4,577,099 A | * | 3/1986 | Goodman ..................... | 250/216 |
| 4,647,544 A | * | 3/1987 | Nicoli et al. .................. | 436/518 |
| 4,692,603 A | | 9/1987 | Brass et al. | |
| 4,728,783 A | | 3/1988 | Brass et al. | |
| 4,745,269 A | | 5/1988 | Van Gils | |
| 4,754,127 A | | 6/1988 | Brass et al. | |

(Continued)

FOREIGN PATENT DOCUMENTS

| | | |
|---|---|---|
| DE | 10348283 A1 | 5/2005 |
| DE | 10360786 B4 | 7/2005 |

(Continued)

OTHER PUBLICATIONS

Bar Code 1 2-Dimensional Bar Code Page; http://www.adams1.com/pub/russadam/stack.html, Adams Communications, pp. 1-11, 1995-2005.

(Continued)

*Primary Examiner* — Daniel Hess
*Assistant Examiner* — Paultep Savusdiphol
(74) *Attorney, Agent, or Firm* — Krieg DeVault LLP

(57) ABSTRACT

An arrangement is provided for reading information from a disposable with an information carrier which comprises a code formed by graphic symbols for the machine-readable provision of information and an optical reading device for the code which has a light source and a sensor. Generally according to the embodiments of the present invention, the information carrier comprises a code applied to a transparent or translucent substrate which can be read under stationary transillumination by means of the light source as a shadow image projected onto the sensor.

32 Claims, 4 Drawing Sheets

U.S. PATENT DOCUMENTS

| | | | |
|---|---|---|---|
| 4,782,221 A | 11/1988 | Brass et al. | |
| 4,786,792 A | 11/1988 | Pierce et al. | |
| 4,794,239 A | 12/1988 | Allais | |
| 4,874,936 A | 10/1989 | Chandler et al. | |
| 4,896,029 A | 1/1990 | Chandler et al. | |
| 4,939,354 A | 7/1990 | Priddy et al. | |
| 4,998,010 A | 3/1991 | Chandler et al. | |
| 5,053,609 A | 10/1991 | Priddy et al. | |
| 5,118,369 A | 6/1992 | Shamir | |
| 5,124,536 A | 6/1992 | Priddy et al. | |
| 5,128,526 A | 7/1992 | Yoshida | |
| 5,153,418 A | 10/1992 | Batterman et al. | |
| 5,189,292 A | 2/1993 | Batterman et al. | |
| 5,198,369 A * | 3/1993 | Itoh et al. | 436/534 |
| 5,203,591 A | 4/1993 | Treat | |
| 5,205,552 A | 4/1993 | Green, Jr. | |
| 5,223,701 A | 6/1993 | Batterman et al. | |
| 5,228,972 A * | 7/1993 | Osaka et al. | 204/415 |
| 5,235,172 A | 8/1993 | Oehlmann | |
| 5,243,655 A | 9/1993 | Wang | |
| 5,245,165 A | 9/1993 | Zhang | |
| 5,281,395 A * | 1/1994 | Markart et al. | 422/82.05 |
| 5,343,031 A | 8/1994 | Yoshida | |
| 5,369,261 A | 11/1994 | Shamir | |
| 5,393,967 A | 2/1995 | Rice et al. | |
| 5,481,103 A | 1/1996 | Wang | |
| 5,554,841 A | 9/1996 | Kost et al. | |
| 5,569,607 A | 10/1996 | Simon et al. | |
| 5,591,956 A | 1/1997 | Longacre, Jr. et al. | |
| 5,612,524 A | 3/1997 | Sant'Anselmo et al. | |
| 5,726,435 A | 3/1998 | Hara et al. | |
| 5,786,584 A * | 7/1998 | Button et al. | 235/462.15 |
| 5,825,015 A | 10/1998 | Chan | |
| 5,989,917 A * | 11/1999 | McAleer et al. | 436/46 |
| 6,016,961 A | 1/2000 | Hippenmeyer et al. | |
| 6,070,805 A | 6/2000 | Kaufman et al. | |
| 6,119,071 A | 9/2000 | Gorenflo et al. | |
| 6,121,599 A | 9/2000 | Traber | |
| 6,176,119 B1 * | 1/2001 | Kintzig | 73/53.01 |
| 6,234,392 B1 * | 5/2001 | Murakami | 235/462.12 |
| 6,260,763 B1 | 7/2001 | Svetal | |
| 6,378,702 B1 * | 4/2002 | Kintzig | 206/456 |
| 6,413,213 B1 * | 7/2002 | Essenpreis et al. | 600/300 |
| 6,460,770 B1 | 10/2002 | Kucharczyk | |
| 6,669,092 B2 | 12/2003 | Leanheart et al. | |
| 6,770,487 B2 * | 8/2004 | Crosby | 436/518 |
| 6,780,645 B2 * | 8/2004 | Hayter et al. | 436/8 |
| 6,883,711 B2 | 4/2005 | Patton | |
| 6,981,644 B2 | 1/2006 | Cheong et al. | |
| 6,988,996 B2 * | 1/2006 | Roe et al. | 600/584 |
| 7,020,327 B2 | 3/2006 | Tack-don et al. | |
| 7,128,265 B2 * | 10/2006 | Silverbrook et al. | 235/462.08 |
| 7,131,596 B2 * | 11/2006 | Lapstun et al. | 235/494 |
| 7,267,799 B1 * | 9/2007 | Borich et al. | 422/82.05 |
| 7,487,914 B2 | 2/2009 | Yoon et al. | |
| 7,717,863 B2 * | 5/2010 | Freeman et al. | 600/583 |
| 7,803,318 B2 * | 9/2010 | Hubner et al. | 422/58 |
| 7,841,992 B2 * | 11/2010 | Freeman et al. | 600/583 |
| 7,850,622 B2 * | 12/2010 | Freeman et al. | 600/583 |
| 7,892,183 B2 * | 2/2011 | Boecker et al. | 600/583 |
| 7,901,362 B2 * | 3/2011 | Freeman et al. | 600/583 |
| 7,981,055 B2 * | 7/2011 | Freeman et al. | 600/583 |
| 8,016,774 B2 * | 9/2011 | Freeman et al. | 600/583 |
| 2001/0042789 A1 | 11/2001 | Krichever et al. | |
| 2001/0045355 A1 * | 11/2001 | Gephart et al. | 204/400 |
| 2002/0030817 A1 | 3/2002 | Matsumoto | |
| 2004/0195330 A1 * | 10/2004 | Silverbrook et al. | 235/454 |
| 2004/0195341 A1 * | 10/2004 | Lapstun et al. | 235/494 |
| 2004/0241752 A1 * | 12/2004 | Anderson et al. | 435/7.1 |
| 2005/0187444 A1 * | 8/2005 | Hubner et al. | 600/322 |
| 2007/0025877 A1 * | 2/2007 | Hansen | 422/68.1 |

FOREIGN PATENT DOCUMENTS

| | | |
|---|---|---|
| DE | 102004051124 B3 | 12/2005 |
| EP | 1424040 A1 | 6/2004 |
| EP | 1 826 705 A1 | 8/2007 |
| JP | 59121578 | 7/1984 |

OTHER PUBLICATIONS

International Search Report and Written Opinion, PCT/EP2007/001605, F. Hoffmann-LaRoche AG, The International Searching Authority/European Patent Office, Jul. 23, 2007.

European Search Report, EP1826705A1, Application No. EP06003880, F. Hoffmann-LaRoche AG, Sep. 21, 2006.

Bar Code 1 2-Dimensional Bar Code Page; http//www.adams1.com/pub/russadam/stack.html, Adams Communications, pp. 1-11, 1995-2005.

* cited by examiner

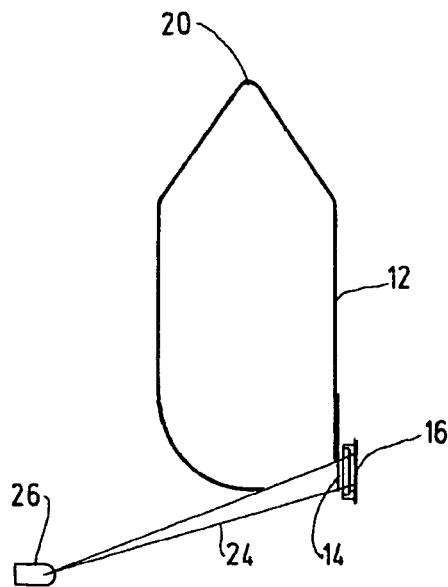
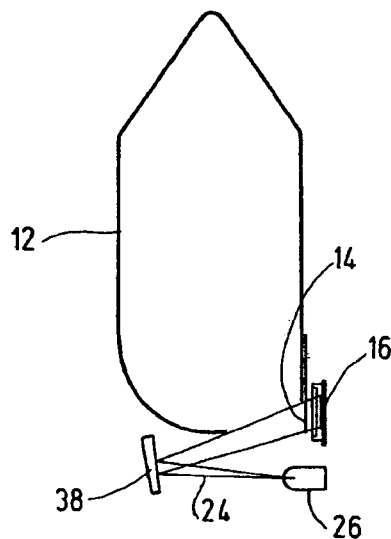
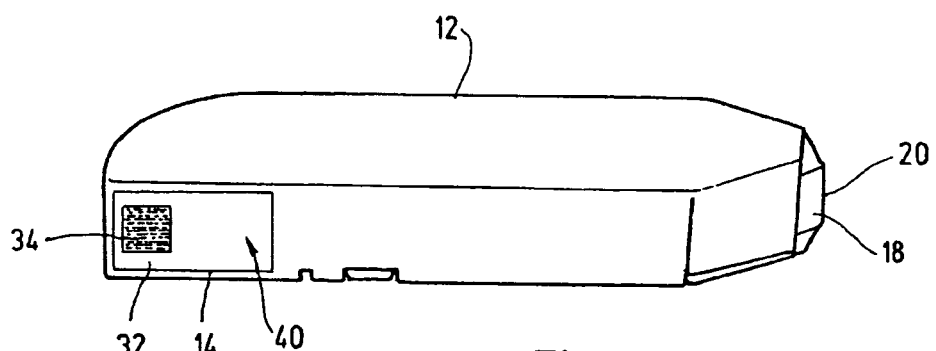
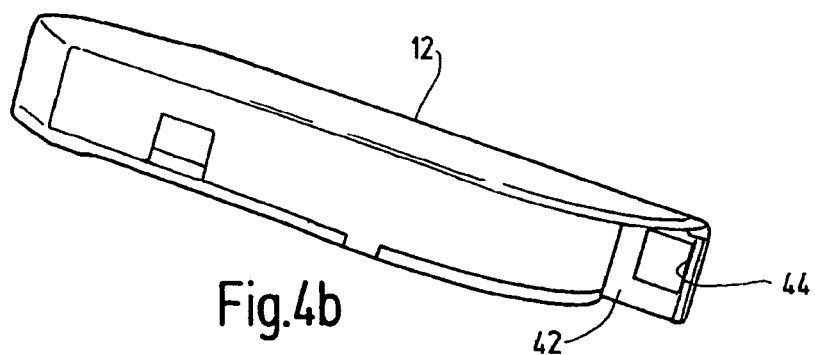

ANALYTE DISPOSABLE MEANS AND DEVICE FOR READING INFORMATION

CLAIM OF PRIORITY

The present application is based on and claims priority to PCT Application No. PCT/EP2007/001605, filed Feb. 23, 2007, which claims the priority benefit to European Application No. 06003880.9, filed Feb. 25, 2006, each of which are hereby incorporated by reference in their entireties.

TECHNICAL FIELD OF THE INVENTION

The present application relates to an analytical disposable or consumable for an analytical system, such as a portable blood glucose measuring device, comprising at least one test unit for applying a sample and an information carrier, and more particularly to an analytical system comprising at last one test unit for applying a sample and an information carrier comprising a code formed by graphic symbols for the machine-readable provision of test-specific information to the device. The invention additionally relates to an arrangement for reading out test-specific information provided on a disposable from an information carrier which comprises a code formed by graphic symbols for the machine-readable provision of information, and an optical reading device for the code which has a light source and a generally flat sensor.

BACKGROUND

A code is usually used when information has to be passed on together with an object. If the object is automatically handled in any manner, then machine-readable codes are typical. Codes that can be read out optically are useful because the codes can typically be inexpensively and rapidly produced by printing processes. Simple machine-readable symbols comprise fields having a sufficiently high contrast between them. Whereas a single black or white field only has an information content of 1 bit, the necessity of having to make larger amounts of information machine-readable led to the development of so-called barcodes. These are lines or bars which, in a defined width and with a defined spacing between each other, can code a certain limited amount of data. The need for transmitting larger amounts of data led to the development of two-dimensional codes (2D-codes). These differ with regard to the amount of data, the size, the necessary contrasts and the requirements with regard to printing quality or reading performance. In the field of analytics such information carriers can be used to provide lot-specific information such as the relationship between analyte and measurement signal in a machine-readable manner. An example of this is the test strip drum of the ACCU-CHEK® Compact blood glucose measuring system available from the Applicant hereof on which a barcode containing test-specific information is provided on the drum and automatically read out, such as is described in DE 10360786, the disclosure of which is hereby incorporated by reference herein in its entirety.

In this context, the object of the present invention is to further improve the means and systems known in the prior art and in particular to ensure a reliable coding and evaluation using simple means.

SUMMARY

This object and others that will be appreciated by a person of ordinary skill in the art have been achieved according to the embodiments of the present invention disclosed herein. In one embodiment, the present invention comprises a code that is position-tolerant with regard to the readout. Accordingly it is proposed that the code has a base code area containing the information and at least one copy code area which comprises a copy of the information from at least a section of the base code area. In one embodiment, the copy code area directly adjoins the base code area. In this manner it is possible to completely detect the code on a limited sensor area even if there are large tolerances in their positions relative to one another. This is especially the case for compact hand-held devices in which analytical disposables can be replaced by the user. The position-tolerant code enables smaller and thus inexpensive sensor components to be used. It is also possible to use simpler and low-cost manufacturing processes for the information carriers, for their application to the disposables and for the devices for holding the disposables.

In one embodiment, a generally square base code area is framed by several copy code areas such that X, Y tolerances can be compensated when reading out the code area. This can be advantageously achieved by making the copy code areas generally vertically and/or generally horizontally and/or generally diagonally displaced relative to the base code area where the displacement distance may correspond to the dimension (width or height) of the base code area in the direction of the displacement.

In other embodiments, the copy code areas adjoin the edges of the base code area without overlap, and are optionally separated by a quiet zone.

In one embodiment, each copy code area is a substantially complete image of the base code area. If the position tolerances are limited, it is alternatively also possible that the copy code areas are formed by code segments or sections of the base code area where the code segments contain at least one edge section of the base code area.

In order to be able to detect the edges of the code even without quiet zones, it is possible to provide the copy code areas alternately in an inverted and non-inverted form, starting from the base code area.

In other embodiments, the code has matrix-like symbols formed by optically distinguishable modules, such as light and dark modules. This enables the efficient provision also of large amounts of data on a small area. In yet other embodiments, the code comprises an information content of at least 100 bit, and even at least 500 bit, such as from a 2D matrix code.

In order to reduce the constructional complexity of the reader, in other embodiments the code is applied to a transparent support and can be read under transillumination as a shadow image on a sensor surface.

In yet other embodiments, the code can be detected by an optical reading system that operates reflectively. In this case the code should be applied to a regular (specular) reflecting substrate so that the light is at least mainly reflected in a directed manner and there is no diffuse reflection or remission such as that which for example occurs on a white pigmented foil or coating.

In order to also compensate for angular deviations, the size of the base code area can be provided at about 0.5-fold to about 1.0-fold the size of the receiving area of a reading device which detects the code.

Another embodiment envisages that the code contains alignment patterns on its edge and/or inside, such as in the form of rows and/or columns.

In one embodiment, the test unit is formed by a section of a test tape in which the information carrier is applied to a tape cassette containing the test tape. It is also conceivable to apply such information carriers to individual test elements, such as to test strips for body fluids.

In other embodiments, the information carrier has a code applied to a transparent substrate which can be read under stationary transillumination by means of the light source as a shadow image on the sensor. As a result the number of components is minimized. No scanners with a scanning movement are required due to the spatial stationary illumination. This also considerably improves the mechanical complexity and the reading reliability. Compared to the conventional use of cameras, complicated components such as lenses, diaphragms and tubes as well as their holders are unnecessary due to the direct optical contact by the shadow image, and the camera distance required for a sharp image is saved. Moreover, a high resolution can also be achieved even at a low illumination level which enables finer codes with higher information densities to be used.

The arrangement according to the present invention tolerates comparatively large deviations of the position of the code relative to the sensor. This enables a more economic manufacture of a device in which a disposable with such a code is handled, due to the less stringent tolerances. It also allows a more economic production of the disposable provided with the code due to the less stringent tolerances. The high quality of the imaging of the code also allows a lower precision in the construction of the code. As a result more economic and in particular more rapid and coarser scanned production processes are acceptable for the code production.

In one embodiment, a sharp shadow image is achieved by arranging the information carrier at a distance of less than about 5 mm from the sensor. In other embodiment, the carrier can be arranged in direct contact with the sensor. A further improvement in this regard results from providing a light source in the form of a point light source (punctiform light source or point radiator), such that the radiated path between the light source and the information carrier is at least 5-times larger than the distance between the information carrier and the sensor.

In order to save constructional space, in other embodiments it is also possible that the light path between the light source and information carrier is folded by a mirror or an optical system.

Generally, the entire area of the code is uniformly transilluminated by a beam of rays originating from the light source.

The code can be formed by a one-dimensional barcode or by a two-dimensional matrix code.

In order to allow a separate production, the information carrier can be affixed to the disposable like a label in which case the disposable has an aperture in the area where the code is affixed.

Alternatively it is also possible that the information carrier is designed as an integral part of the disposable where the substrate is formed by a wall area of the disposable that is transparent to the radiation used for the readout.

In one embodiment, the sensor is formed by a CMOS sensor or a CCD sensor where the light-sensitive sensor surface comprises a plurality of pixels.

In other embodiments, the reading device is configured as a part of a device designed to exchange the disposable.

In order to compensate for positioning tolerances between the reading device and the information carrier, in other embodiments the reading device comprises a flexible and/or elastic mounting for the sensor.

A further constructional realization provides that the light source has a light guide extending into the interior of the disposable and that the sensor is arranged outside the disposable.

The present invention also relates a system comprising a combination of a disposable and an information reading device in which particular advantages are achieved for its accommodation in a device especially with regard to the reduced constructional complexity and the positioning tolerances.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which:

FIGS. 3 and 4 show further arrangements of a reading device on a disposable cassette in a diagram corresponding to FIG. 1.

FIGS. 4a and b show the disposable cassette according to FIG. 1 in two perspective views of the narrow side.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
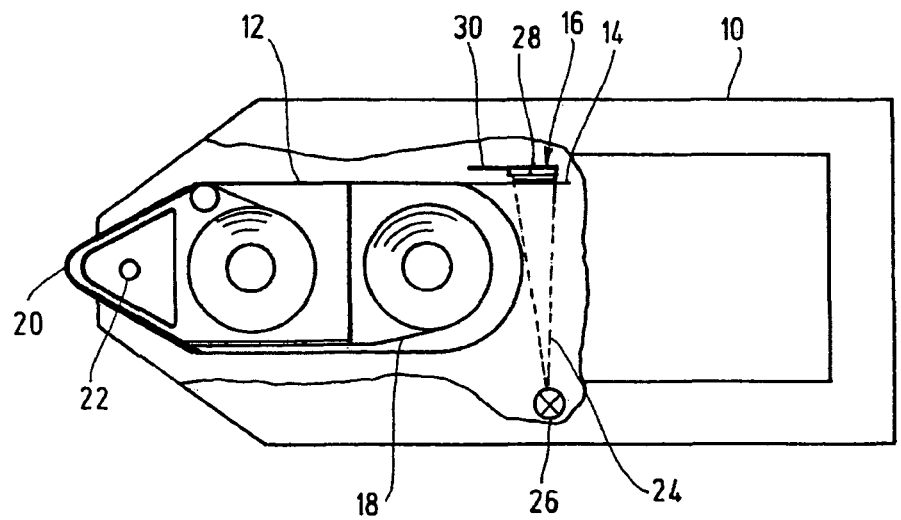
FIG. 1 shows a measuring device with a replaceable disposable cassette and an optical reading device for an information carrier on the cassette in a partially cut-out side-view.

The exemplary measuring device 10 shown in FIG. 1 enables the use of a test tape cassette 12 as an analytical disposable for carrying out, in this embodiment, blood glucose tests in which test-specific information on an information carrier 14 on the cassette 12 can be read out by means of the device's own reading device 16.

The test tape cassette 12 contains a test tape 18, sections of which are provided with test fields to which blood can be applied to a tip 20 protruding from the device 10 in order to locally determine a blood glucose value by means of the measuring device 22. A plurality of tests can thus be carried out by winding on the test tape 18, before the cassette 10 is used and has to be replaced. Reference is for example made to EP 1424040 and DE 10348283 with regard to further details of such hand-held devices, the disclosures of which are hereby incorporated by reference herein in their entireties.

In principle, the use of the information carrier and the associated reading device described here is not restricted to such test tape cassettes. Other diagnostic or analytical test units can also be provided with them and in particular also test strips such as those that are currently used to examine body fluids. Their use is also advantageous in other medical disposables e.g. dialysers, tube sets, infusion containers and suchlike which are used in devices and also for disposables in other fields of application such as for example colour, printing, lubricant or additive cartridges, grinding or cutting implements, sample or tool carriers, moulds or receivers such as e.g. printing screens.

Figure 2:
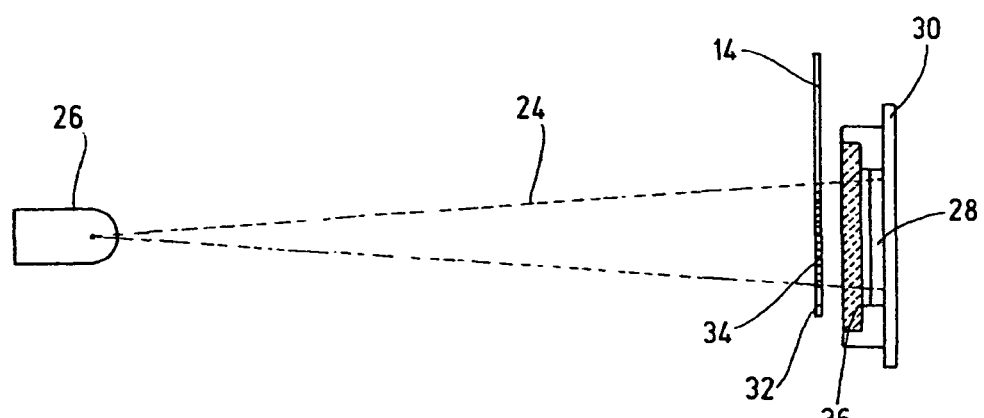
FIG. 2 shows an enlarged diagram of the reading device and the information carrier according to FIG. 1.

As shown in FIGS. 1 and 2, the information carrier 14 as part of the cassette 10 is located in the optical path (light beam 24) of the reading device 16. This device comprises a light source 26 and a generally flat sensor 28 on a circuit board of the device 30. In order to make the system as simple as possible, a scanning relative movement of the reading light and the information carrier 14 is not employed and instead a simple shadow image of the code on the information carrier is detected. For this purpose the information carrier 14 comprises a substrate 32 which is generally transparent or translucent to the light beam and a graphic code 34 applied thereto which is described in more detail below. This code is thrown as a shadow image through the entry window 36 onto the receiving surface of the sensor 28 when it is read by the stationary i.e. spatially unmoved light beam 24 without using an imaging optical system.

In order to in this case achieve the highest possible resolution, the light source 26 comprises a point light source and is arranged at a large distance to the information carrier 14 compared to its distance from the sensor 28, where in the latter case it is desirable to have a direct contact between the substrate 32 and entry window 36.

A point light source 26 is typically regarded as a light source which is characterized by small dimensions of the light-emitting area, or which has comparable emission characteristics as a result of optical elements. Light-emitting diodes (LED) are typically suitable for this, but filament lamps, laser diodes, gas discharge lamps and suchlike as well as light guides can also be used in a suitable configuration. The wavelength of the light for illumination is generally only limited by the sensitivity of the optical sensor and the material properties of the information carrier 14. Visible light can be used, including red light, because the most cost-effective LEDs operate in this wavelength range.

The smaller the dimensions and the larger the distance of the light source 26, and the smaller the distance of the sensor 28 from the information carrier 14, the sharper will be the image of the code module on the surface of the sensor 28. A sharp image enables a reliable detection already at a low over-sampling. Over-sampling denotes the multiple of pixels which is required to reliably detect a code element. Single over-sampling means that one pixel per code element is available on the sensor. Double over-sampling means that two pixels are available for each edge length or line thickness of the code 34. The higher the chosen over-sampling, the lower are the required imaging qualities and position accuracies for a reliable reading. However, the number of pixels increases quadratically with the over-sampling. Thus, the amount of data that has to be read, stored and processed also increases. This generally requires hardware components of an adequate size as well as longer processing times and/or faster processors.

In one embodiment, the light-sensitive sensor comprises a CMOS sensor; alternatively a CCD sensor can also be used. The light-sensitive surface of such sensors generally comprises a plurality of pixels which individually record the local brightness. When the code 34 is illuminated by the point light source 26, the modules or elements of the code 34 impede the passage of light whereas the light impacts the light-sensitive sensor 28 almost unhindered through the transparent/translucent substrate 32. The differences in brightness generated in this manner are read by electronics of the reading device 16 and can be processed to form a total image of the code 34. The electronics can also comprise components for further image processing in order to decode the code 34 into alphanumeric characters.

The position of the code 34 relative to the sensor 28 can tolerate relatively large deviations. The deviations in the direction of the width and the height of the code can be compensated by selecting a light-sensitive area of the sensor 28 which is enlarged compared to the code. The effect of deviations in the distance between the code 34 and the sensor 28 can be kept small by the small dimensions and a large spacing of the point light source 26 and the omission of distorting optical components in the light path.

In order to further reduce the positioning tolerances, the sensor assembly 28, 36 can be seated in a flexible mounting 30. This minimizes deviations in the lateral position and level of the information carrier 14 so that a smaller light-sensitive area of the sensor 28 is sufficient. In particular a spring mounting enables a contact between the information carrier 14 and the surface of the sensor 28 without the risk of damage even when the cassette 12 is inserted into a device holder that has tolerances.

As described above the point light source 26 may be positioned at a large distance from the information carrier 14. In this connection it has turned out that an orthogonal alignment relative to the sensor area is necessary. In accordance with FIG. 3*a* the light source 26 can also be laterally displaced thus enabling a useful exposure to light without interfering contours occurring due to the disposable 12. As shown in FIG. 3*b* the incident path of the light beam 24 can be folded by a mirror 38 or another suitable optical element in order to minimize the overall length of the device. Such an optical element can also have imaging properties which form a virtual point light source from an expanded light source.

As shown in FIG. 4*a* the information carrier 14 can be glued onto the cassette 12 in the form of an adhesive label 40. The adhesive area can be omitted in the area of the code 34 or a transparent adhesive is used. The rear view of FIG. 4*b* shows that a window or an opening 44 spanned by the label 40 is provided in a projecting support tab 42 of the cassette 12 and thus allows an unhindered illumination of the code 34 from the rear side in the configurations shown in FIG. 3.

In principle it is also possible that the light source 26 is effectively positioned within the object to be coded for example by using optical elements such as light guides for a suitable light guidance. It is also conceivable that a wall of the object is made as transparent or translucent as the substrate 32 thus enabling a transillumination of the code 34.

The code 34 can thus be generated on the object 12 to be coded itself or on a label 40 which is joined to the object 12 in the production process. Printing processes such as thermotransfer printing, screen printing, offset printing, laser printing and inkjet come into consideration for the production of the code 34. In addition laser engraving, laser ablation, film exposure and development, sputtering, sublimation processes and other suitable processes can also be used. The contrast for displaying the code 34 can thus be generated by dyes or pigments such as those contained in printing colours or photographic films, by metal layers, by changes in materials such as colouration, charring, by light-scattering phase interfaces (e.g. pores) or in other suitable ways. The code can either be configured as a positive with dark modules or inverted as a negative with transparent modules. The code can be a one-dimensional or two-dimensional barcode, line code, point code or a derivative thereof. A so-called data matrix code (ECC200) is preferably used in the embodiment described in the following. Further details on data matrix codes can for example be found in the U.S. Pat. Nos. 4,939,354; 5,053,609; 5,124,536; the disclosures of each of which are hereby incorporated herein by reference.

Figure 5:
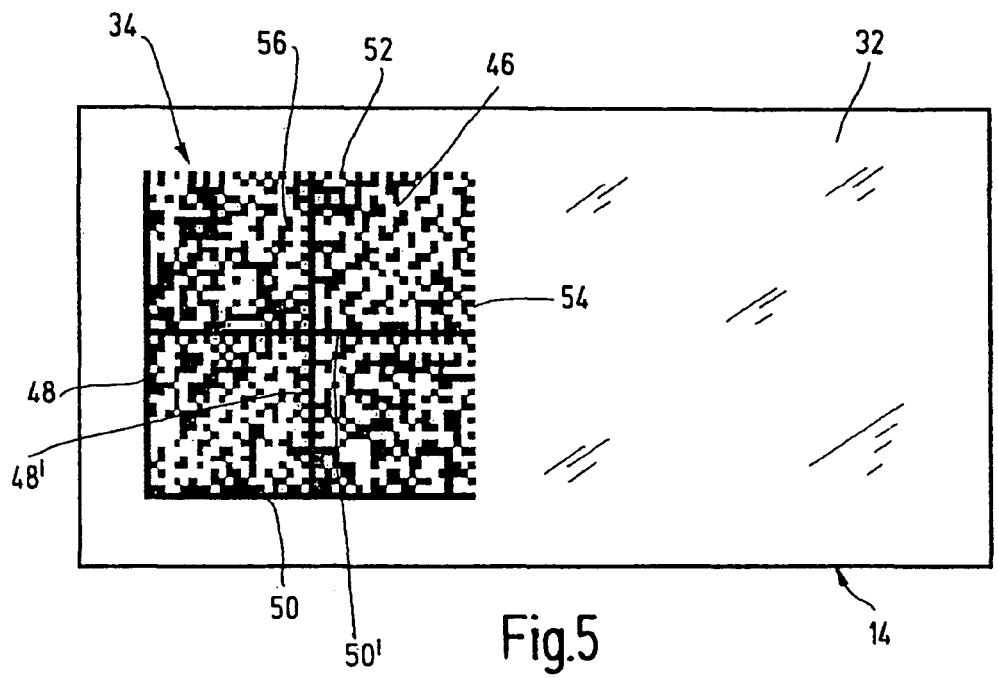
FIG. 5 shows an information carrier comprising a transparent substrate and a two-dimensional data matrix code.

FIG. 5 shows an information carrier 14 comprising a transparent or translucent substrate 32 and a two-dimensional graphic code 34 in the form of a data matrix code that is applied thereto. This code comprises a quadratic matrix of dark grid modules 46. In order to determine the orientation and density of the modules, a continuous dark line 50 or column 48 is provided on two adjoining edges or sides of the square whereas the other two edges 52, 54 have alternating dark and light modules where the right upper corner is always light. This so-called alignment pattern can, as shown, also be repeated in the inside of the code area 56 (line 50' or column 48').

Data matrix codes 34 generally have angle tolerance, i.e. they can be read and evaluated when rotated by virtually any angle relative to a reference alignment. When such a code is read in direct contact as described above, it is necessary to use a sensor 28 whose optically sensitive area is larger than the edge length of the code at least by the horizontal and vertical position tolerance. If the sensor is not aligned parallel to the edges of the code then, instead of the edge length of the code, the projection of the diagonals has to be taken into account which is at most 1.41-times the edge length at any angular position. If only small angles of rotation are expected, it is not necessary to completely form an image of the code on the optically sensitive area of the sensor when utilizing the error tolerance of a data matrix code or of a similar code with error correction.

Figure 6:
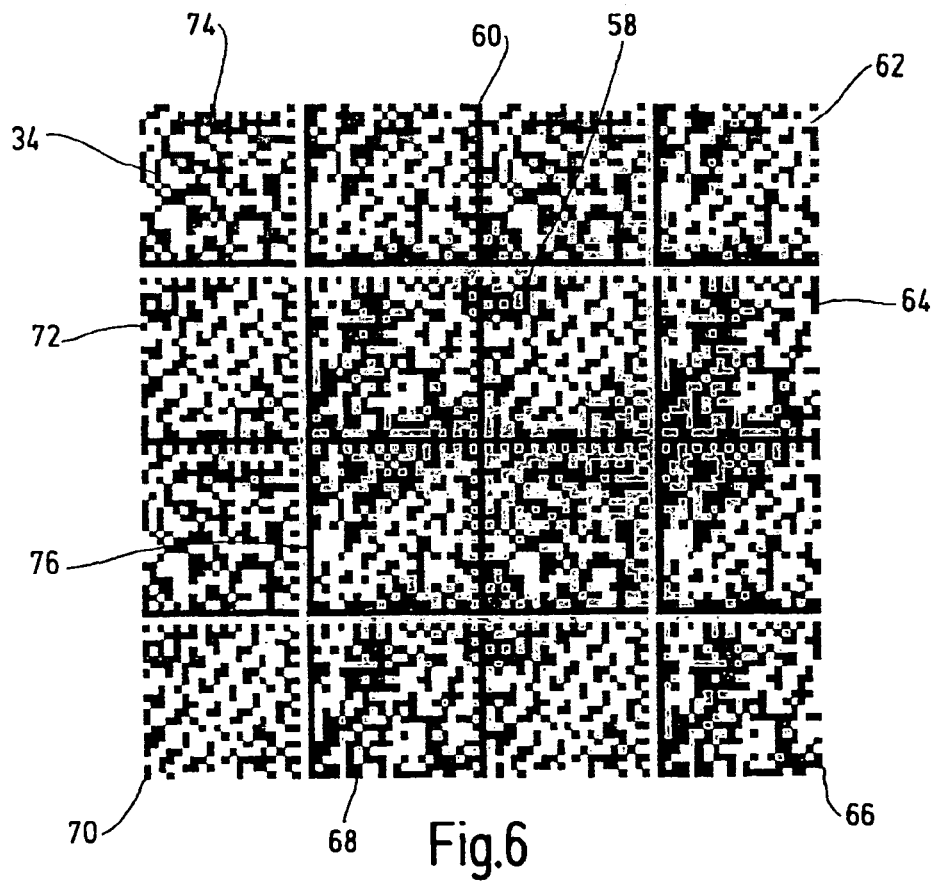
FIG. 6 shows an embodiment of a matrix code with a base code area and bordering copy code areas.

In order to create a position-tolerant code in this connection which can also be reliably read by smaller and thus inexpensive sensors, an extensive code area is provided as shown in FIG. 6. In this case the code 34 has a base code area 58 corresponding to the diagram in FIG. 5 which is framed by several adjacent copy code areas 60, 62, 64, 66, 68, 70, 72, 74. The copy code areas 60-74 are each displaced relative to the base code area 58 only in one direction generally vertically, generally horizontally and/or generally diagonally, only to the extent that they adjoin the borders of the base code without overlap while forming a quiet zone 76 of at least the dimensions (width or height) of a code element. The copy code areas are in this case formed by the border segments of the base code area which face away vertically, horizontally and diagonally. For example the copy code area 60 corresponds to the lower half of the base code area 58 whereas the copy code area 66 corresponds to the left upper quarter of the base code area 58.

Due to the presence of copies of the base code, it is possible for an optically sensitive sensor 28 of the size of the base code area 58 to detect all information of the base code irrespective of the relative deviation in position. This is of course providing that the dimensions of the code 34 are so large that the detection area of the sensor 28 does not extend beyond the edge of the code 34.

The base code is reconstructed by the reading device 16 firstly determining the origin of the coordinate system of the code image. This is firstly explained for an embodiment with a quiet zone. The following convention applies to the explanation. An illuminated pixel yields the value 1, a shaded pixel yields the value 0. Intermediate values are prevented by an upstream discriminator, e.g. a Schmitt trigger.

Firstly all sums of the columns and lines are added up and minima and maxima of the means are determined. These first minima and maxima are brought onto the absolute minima and maxima of the means by incremental virtual rotation of the pixel data. At the origin of the coordinate system of the code image several columns with a maximum value of the column mean adjoined by several columns with a minimum value of the column mean intersect in each case with several lines with a maximum value of the line mean adjoined by several lines with a minimum value of the line mean. The intersection of the crossovers from the minimum value to the maximum value in the relevant columns and lines is the origin. If the reading device 16 identifies more than one such intersection, then the intersection with the smallest x value and the smallest y value of the coordinates on the sensor 28 is determined as the origin of the coordinate system of the code image.

In the code image of FIG. 6 a column or line with alternating light and dark code elements is located next to each of the quiet zones 76. When the base code is reconstructed in a processor (not shown) the average distance between a light/dark transition is determined in the x direction as well as in the y direction. Thus, the number of pixels that correspond to the edge length of a code element is known. Taking into account the determined rotation and the edge length, lines of pixel values are transferred into a complete orthogonally aligned code image in a memory starting at the origin. The decoding algorithms are applied to this virtual code image in order to obtain the code content in a digitally utilizable form.

Figure 7:
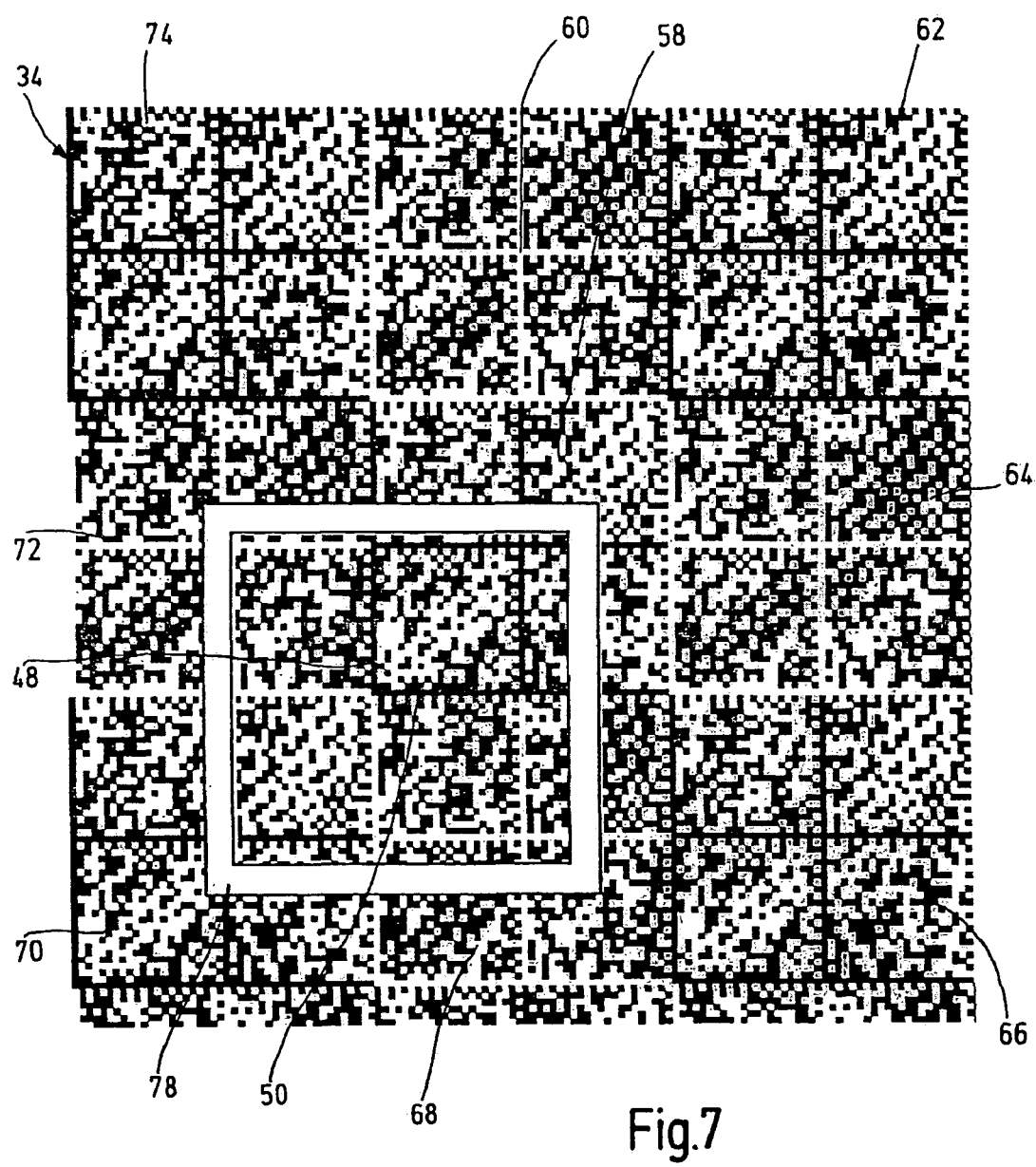
FIG. 7 shows a further embodiment of the matrix code with a base code area and alternating inverted and non-inverted copy code areas and a sensor window of the reading device symbolized therein.

In the embodiment example shown in FIG. 7 the base code area 58 is framed by complete copies 60-74. Starting from the base code area 58, the copies 60-74 are shifted vertically, horizontally and diagonally to such an extent that they exactly join the code edges without gaps and without overlaps. This results in a 2D code with three times the edge length and nine times the area of the base code area 58. In order to be able to simply detect the alignment pattern while avoiding quiet zones, the copies 60-74 are alternately inverted and non-inverted starting from the base code area 58. The copies 60, 64, 68, 72 are referred to as inverted in which the modules that are dark in the original 58 are light and the modules that are light in the original are dark. This thus results in a chessboard-like pattern of non-inverted and inverted base codes.

When the alignment patterns 48, 50 of the base code area 58 are dark, the alignment patterns of the inverted copies are light and are thus clearly distinguishable. Dark angles from the alignment patterns 48, 50 are present at the left lower edge of a non-inverted code area 58, 62, 66, 70, 74. In contrast light angles are present at the left lower edge of an inverted code area 60, 64, 68, 72. Equally there is an intersection of dark lines inside a non-inverted code area and an intersection of light lines inside an inverted code area. There is a dark T-formation at the edge of a non-inverted code area and a light T-formation at the edge of an inverted code area. This information enables the base code area 58 to be reconstructed and provided for the decoding at any position of the sensor 28 shown in FIG. 7 by a reading window 78 provided it does not extend beyond the edge of the code 34.

The code copying according to the invention is not only limited to the contact mode described above, but can also be advantageously used when reading codes 34 by an imaging optical system in order to increase the positioning tolerance. Also in this case it may be necessary when replacing a disposable 12 to exactly position the information carrier to be read within a certain tolerance. Especially in the case of readers that are permanently installed in the device that have to read only a few different code types, the use of the proposed code copies allows the use of smaller and thus less expensive optical sensors.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An analytical system including an analytical disposable, comprising at least one test unit and an information carrier which comprises a two-dimensional code formed by graphic symbols configured for machine-readable provision of test-specific information, and an optical reading device for the two-dimensional code that includes a sensor defining a detection area, wherein the code comprises a base code area containing the information and a generally adjacent copy code area containing a copy of at least a section of the base code area, wherein the copy code area adjoins an edge of the base code area, and the dimensions of the two-dimensional code defined by the copy code area and the base code area are greater than the detection area of the sensor of the optical reading device so that the detection area of the sensor does not extend beyond the edges of the code defined by the base code area and the adjoining copy code area, wherein the two-dimensional code is applied to a transparent or translucent substrate and is readable under transillumination as a shadow image projected onto a flat sensor.

2. The analytical system according to claim 1, wherein the code area comprises a quadratic base code area framed by a plurality of copy code areas.

3. The analytical system according to claim 2, wherein the copy code areas each are displaced one or more of vertically, horizontally and diagonally, relative to the base code area.

4. The analytical system according to claim 2, wherein starting from the base code area, the copy code areas are alternately in an inverted and non-inverted form.

5. The analytical system according to claim 1, wherein the copy code area adjoins the edge of the base code area without overlap and is adjoined by a quiet zone therebetween.

6. The analytical system according to claim 1, wherein each copy code area contains a complete copy of the base code area.

7. The analytical system according to claim 1, wherein the copy code area is formed by code segments of the base code area where the code segments contain at least one edge section of the base code area.

8. The analytical system according to claim 1, wherein the code comprises matrix-like symbols formed by optically distinguishable modules.

9. The analytical system according to claim 1, wherein the code comprises a 2D matrix code having an information content of at least 100 bit.

10. The analytical system according to claim 1, wherein the size of the base code area is generally about 0.5-fold to about 1.0-fold the size of the sensor area of the optical reading device configured to detect the code.

11. The analytical system according to claim 1, wherein the code contains alignment patterns in the form of one or both of rows and columns.

12. The analytical system according to claim 1, wherein the test unit comprises a section of a test tape and the information carrier is applied to a tape cassette containing the test tape.

13. The analytical system according to claim 1, wherein the code comprises a 2D matrix code having an information content of at least 500 bit.

14. The analytical system according to claim 1, wherein the copy code area in combination with at least a portion of the base code area contains substantially the same information at the base code area.

15. The analytical system according to claim 1 comprising a plurality of copy code areas wherein each of said copy code areas in combination with at least a portion of the base code area contains substantially the same information at the base code area.

16. The analytical system according to claim 1 wherein the copy code area is a substantially complete image of the base code area.

17. An arrangement for reading information on a disposable with an information carrier, wherein the arrangement comprises a holder with measuring device and an optical reading device comprising a light source and a sensor, and the disposable comprises a cassette in the holder with a windable test tape having a plurality of test fields movable around the measuring device to determine a blood glucose value, and the information carrier is carried by the cassette and comprises a code formed by graphic symbols configured for machine-readable provision of information, wherein the code is applied to a transparent or translucent substrate and is configured to be read by the optical reading device under stationary transillumination by means of the light source as a shadow image projected onto the sensor.

18. The arrangement according to claim 17, wherein the information carrier is arranged at a distance from the sensor of between about 5 mm and 0 mm, wherein 0 mm includes direct contact with the sensor.

19. The arrangement according to claim 17, wherein the light source is located on the side of the information carrier that faces away from the sensor.

20. The arrangement according to claim 17, wherein the light source comprises a point light source.

21. The arrangement according to claim 17, wherein the light source generates an irradiated path between the light source and the information carrier, and wherein the irradiated path is at least about 5-times longer than the distance between the information carrier and the sensor.

22. The arrangement according to claim 17, wherein a light path generated between the light source and information carrier is folded by one of a mirror and an optical system.

23. The arrangement according to claim 17, wherein the area of the code is generally uniformly transilluminated by a beam of rays originating from the light source.

24. The arrangement according to claim 17, wherein the code comprises one of a one-dimensional barcode and a two-dimensional matrix code.

25. The arrangement according to claim 17, wherein the information carrier is affixed to the disposable like a label and the disposable comprises an aperture in the area where the code is affixed.

26. The arrangement according to claim 17, wherein the information carrier is configured as an integral part of the disposable where the substrate is formed by a transparent or translucent wall area of the disposable.

27. The arrangement according to claim 17, wherein the sensor comprises one of a CMOS sensor and a CCD sensor, and wherein the light-sensitive sensor surface comprises a plurality of pixels.

28. The arrangement according to claim 17, wherein the holder is configured to exchange the disposable.

29. The arrangement according to claim 17, wherein the reading device comprises a flexible spring-mounting for the sensor configured to compensate for positioning tolerances between the reading device and the information carrier.

30. The arrangement according to claim 17, wherein the light source comprises a light guide extending into the interior of the disposable and the sensor is arranged outside the disposable.

31. The arrangement according to claim 17, wherein the disposable can be inserted into the holder and the holder is configured to position the information carrier relative to the arrangement.

32. The arrangement according to claim 31, wherein the holder comprises a portable hand-held device.

* * * * *